US005535006A

United States Patent [19]

Telschow et al.

[11] Patent Number: 5,535,006
[45] Date of Patent: Jul. 9, 1996

[54] METHOD AND SYSTEM FOR EVALUATING INTEGRITY OF ADHERENCE OF A CONDUCTOR BOND TO A MATING SURFACE OF A SUBSTRATE

[75] Inventors: Kenneth L. Telschow, Idaho Falls, Id.; Bernard K. Siu, Diamond Bar, Calif.

[73] Assignee: Lockheed Idaho Technologies Company, Idaho Falls, Id.

[21] Appl. No.: 250,078

[22] Filed: May 26, 1994

Related U.S. Application Data

[63] Continuation-in-part of Ser. No. 25,441, Mar. 1, 1993, Pat. No. 5,420,689, and a continuation-in-part of Ser. No. 25,442, Mar. 1, 1993, Pat. No. 5,424,838, and a continuation-in-part of Ser. No. 914,541, Jul. 16, 1992, Pat. No. 5,302,836.

[51] Int. Cl.$^6$ ................................................. G01B 11/24
[52] U.S. Cl. .................... 356/394; 356/376; 356/237; 250/559.01; 250/559.42
[58] Field of Search ........................... 356/394, 432, 356/376, 237; 73/582, 588; 250/562, 572

[56] References Cited

U.S. PATENT DOCUMENTS

| | | | |
|---|---|---|---|
| 3,978,713 | 9/1976 | Penney | 73/67.7 |
| 4,121,469 | 10/1978 | Kaule et al. | 73/643 |
| 4,129,041 | 12/1978 | Bickel | 73/657 |
| 4,137,778 | 2/1979 | Primbach | 73/627 |
| 4,144,767 | 3/1979 | Kaule et al. | 73/643 |
| 4,169,662 | 10/1979 | Kaule et al. | 350/358 |
| 4,523,469 | 6/1985 | Scott et al. | 73/603 |
| 4,581,939 | 4/1986 | Takahashi | 356/432 |
| 4,641,527 | 2/1987 | Hiroi et al. | 73/582 |
| 4,659,224 | 4/1987 | Monchalin | 356/352 |
| 5,088,327 | 2/1992 | Gammell | 73/582 |
| 5,103,676 | 4/1992 | Garcia et al. | 73/597 |

FOREIGN PATENT DOCUMENTS

| | | |
|---|---|---|
| 62-7198 | 1/1987 | Japan . |
| 2185816 | 7/1987 | United Kingdom . |

OTHER PUBLICATIONS

K. L. Telschow et al., "Laser Ultrasonic Monitoring of Ceramic Sintering", J. Appl. Phys., 68 (12), Dec. 15, 1990. pp. 6077–6081.

Primary Examiner—Robert P. Limanek
Assistant Examiner—David B. Hardy
Attorney, Agent, or Firm—Wells St. John Roberts Gregory & Matkin

[57] ABSTRACT

A method of evaluating integrity of adherence of a conductor bond to a substrate includes: a) impinging a plurality of light sources onto a substrate; b) detecting optical reflective signatures emanating from the substrate from the impinged light; c) determining location of a selected conductor bond on the substrate from the detected reflective signatures; d) determining a target site on the selected conductor bond from the detected reflective signatures; e) optically imparting an elastic wave at the target site through the selected conductor bond and into the substrate; f) optically detecting an elastic wave signature emanating from the substrate resulting from the optically imparting step; and g) determining integrity of adherence of the selected conductor bond to the substrate from the detected elastic wave signature emanating from the substrate. A system is disclosed which is capable of conducting the method.

22 Claims, 12 Drawing Sheets

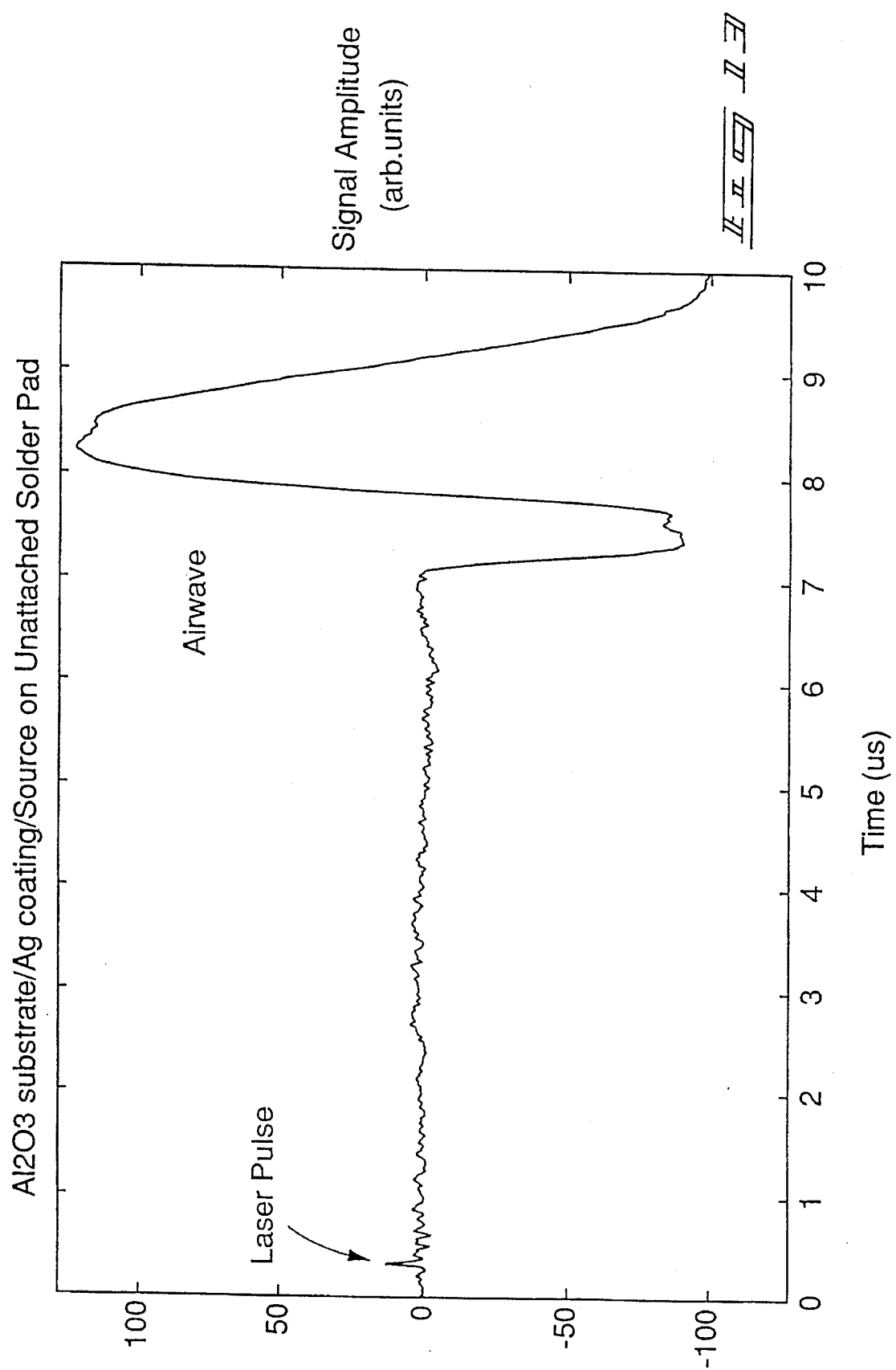

METHOD AND SYSTEM FOR EVALUATING INTEGRITY OF ADHERENCE OF A CONDUCTOR BOND TO A MATING SURFACE OF A SUBSTRATE

CONTRACTUAL ORIGIN OF THE INVENTION

The United States Government has rights in this invention pursuant to contract No. DE-AC07-76ID01570 between the United States Department of Energy and EG&G Idaho, Inc.

RELATED PATENT DATA

This patent resulted from a continuation-in-part application of U.S. patent application Ser. Nos. 08/025,441 and 08/025,442, both filed on Mar. 1, 1993, and entitled "High Speed Illumination System For Microelectronics Inspection" and "High Speed System For Microelectronics Inspection" respectively, and which are U.S. Pat. Nos. 5,420,689 and 5,424,838, respectively; and of U.S. patent application Ser. No. 07/914,541, filed on Jul. 16, 1992, entitled "High Speed Image Acquisition For Microelectronics Inspection", and which is U.S. Pat. No. 5,302,836. Each of these prior applications is hereby incorporated by reference as if fully set forth in this document.

TECHNICAL FIELD

This invention relates to the evaluation of the integrity of adherence of a conductor bond to a mating surface on a substrate.

BACKGROUND OF THE INVENTION

With the advancements in manufacturing technologies and miniaturization of electronics packaging, the military and commercial industry has enjoyed many advantages over the past 15 to 20 years using electronic and microelectronics design and packaging techniques. The use of microelectronics packaging techniques has allowed military and other users to increase their system complexities and hardware performance, but at the same time, reduce their size and weight requirements. This packaging trend is unlikely to stop and the miniaturization technology undoubtedly will continue.

As manufacturing techniques for microelectronics assemblies advance, hardware density and complexity are pushed to practical limits. Production yields and hardware reliability are heavily dependent on the dimensional, positional and attachment feedback throughout the manufacturing process. The lack of real-time, high resolution, non-contact sensors dictates that quality assurance check points have to be placed at the end of manufacturing cycles and processes, so that actual quality of the hardware produced can be verified or inspected.

Industry responded to the above challenge by developing and implementing automated manufacturing and inspection machines to minimize quality assurance costs with more consistent results. Though with some significant accomplishments, there are many challenges ahead. For example quality standards such as Mil-Std-883, Mil-H-38534 and others were designed and written specifically to govern the universal manufacturing quality of microelectronics and electronic hardware. Most of these quality standards require visual verification of the dimension, shape, physical configuration as well as appearance of the part under test. Due to the size, complexity and fragility of the materials used, these quality standards cannot always be accurately measured or pin-pointed by a human operator or existing sensors. Nor can they be sensed during the manufacturing cycle to support real-time feed back loops for process control.

As an example, one pass/fail criteria concerns attachment or bonding integrity of features such as ball bonds, wedge bonds or solder joints. The existence of balls, wedges and other conductor bonds might be detectable by machine vision sensors with acceptable speed and resolution for process control. However, the integrity of such bonds cannot in any practical sense be evaluated or analyzed by visual inspection means. Microcircuit bonding quality checks today are generally performed using bond pull and bond shear techniques and machines. The bond shear test is a destructive test which cannot be used on functional bonds. The bond pull test requires a controlled pull force to ensure no damaging effect on the bond wires. Both of these approaches require the use of contact type sensors which are slow, labor intensive and above all, change the original configuration of the bond wires being tested. In addition, these techniques cannot be used to support real-time process control on high speed manufacturing tasks.

Further while these techniques may have been acceptable in past years, they are not capable of keeping up with the rest of today's and future high speed manufacturing processes. Additionally, visual inspection is not a most effective technique for detecting delamination between material layers or attachment integrity of bonding materials, such as ball bonds, trace attachments, etc. The above labor intensive inspection efforts and human judgment calls are major contributors to the "cost of quality" of electronic products today.

It would be desirable to develop automated, non-contacting methods and equipment for evaluating the integrity of electronic, and even more specifically microelectronic, conductor bonds to substrates, such as to electronic and microelectronic integrated circuitry formed within a semiconductor substrate, as well as soldering joints or other conductor bonds. This invention spawned out of needs and concerns associated with the electronics and microelectronics industry, and specifically to the evaluation of ball bonds and wedge bonds in the microelectronics industries. However, the artisan will appreciate that the invention may have utility in evaluating integrity of other conductor bonds.

BRIEF DESCRIPTION OF THE DRAWINGS

Preferred embodiments of the invention are described below with reference to the following accompanying drawings.

FIG. 13 is a plot of signal amplitude vs. time, as was experimentally reported, in analysis of the FIG. 12 test.

DETAILED DESCRIPTION OF THE PREFERRED EMBODIMENTS

Figure 1:
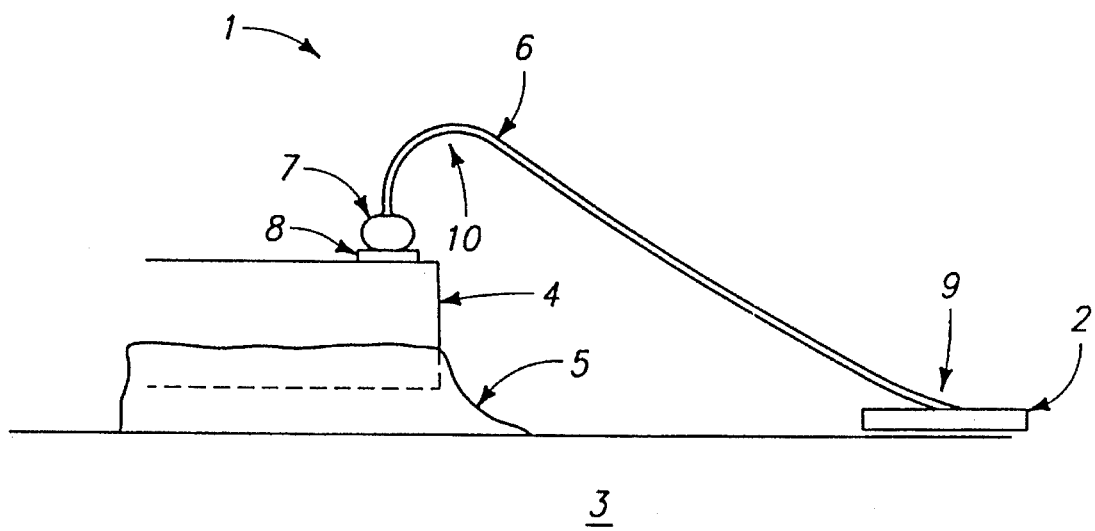
FIG. 1 is a partial side elevational view of a microelectronics assembly, showing a typical interconnection between a microcircuit chip and a conductor trace on a substrate.

This disclosure of the invention is submitted in furtherance of the constitutional purposes of the U.S. Patent Laws "to promote the progress of science and useful arts" (Article 1, Section 8).

In accordance with one aspect of the invention, a method of evaluating integrity of adherence of a conductor bond to a mating surface on a substrate comprises the following steps:

impinging a plurality of light sources onto a substrate;

detecting optical reflective signatures emanating from the substrate from the impinged light;

determining location of a selected conductor bond on the substrate from the detected reflective signatures;

determining a target site on the selected conductor bond from the detected reflective signatures;

optically imparting an elastic wave through the selected conductor bond and into the substrate;

optically detecting an elastic wave signature emanating from the substrate resulting from the optically imparting step; and determining integrity of adherence of the selected conductor bond to the substrate from the detected elastic wave signature emanating from the substrate.

In accordance with another aspect of the invention, a system for evaluating integrity of adherence of a conductor bond to a mating surface on a substrate comprises:

a plurality of light sources to illuminate a substrate and components adhered thereto;

photodetector means for detecting reflective signatures emanating from the substrate resulting from operation of the light sources;

locating means for determining location of a selected conductor bond on the substrate from detected reflective signatures;

targeting means for determining a target site on the selected conductor bond;

wave propagation means for optically imparting an elastic wave at the target site through the selected conductor bond and into the substrate;

aiming means for aiming the wave propagation means and substrate relative to one another for imparting the elastic wave onto the target site of the selected conductor bond;

optical detection means for detecting an elastic wave signature emanating from the substrate resulting from operation of the wave propagation means; and processor means for determining integrity of adherence of the selected conductor bond to the substrate from the detected elastic wave signature emanating from the substrate.

This disclosure also relates, in part, to an improved system for visual inspection of electronic and microelectronic assemblies, including interconnect wires, ball bonds, wedge bonds, solder joints and other conductor connections contained therein, and the location of such connections for aiming of elastic wave generation apparatus onto such connections. The discussion starts with description of the visual inspection system aspect of this and the parent disclosures. Such is initially utilized to determine the existence and alignment of desired components on a manufactured and bonded surface. Such will also be used in locating conductor bonds of interest for bond integrity analysis in accordance with the invention, which is described subsequently.

Visual inspection of electronic devices today often uses a comparative method. Magnified projections of a reference sample and of the unit under inspection are visually compared on adjacent or split screens. The human inspector visually does the comparison and makes a subjective pass or fail judgment based upon their experience and training. The method is time consuming and produces inconsistent inspection results.

Replacement of the human operator with an automatic inspection machine as provided in the parent disclosures involves overcoming three obstacles. The first obstacle is to be able to "see" and isolate objects of interest from their background. For instance, gold wires, gold wire bonds, and gold wedges must be identified against gold or similar backgrounds in a manner somewhat similar to that used by a human inspector. The second obstacle is to acquire the image and make pass or fail decisions based upon perceptions of the acquired image. A third obstacle is to repeatedly solve the first two problems at a rate beyond the capability of the human operator.

Automatic testing of bonding integrity in accordance with this disclosure also involved overcoming obstacles. For example, the same first obstacle of being able to "see" and isolate objects of interest from their background is present. A second obstacle is to acquire an image and determine the exact target site on the object of interest such that the intended energy source can be pinpointed appropriately. A third obstacle is to optically direct the energy to strike the target with high precision. A fourth obstacle is to impart and detect an elastic wave signature emanating from the substrate resulting from the energy imparting step.

An initial part of the following disclosure principally relates to the parent disclosures, and comprises the combination of a high speed illumination apparatus with a novel image capture subsystem and with other necessary elements for defect fault diagnosis. Preferred apparatus generates multiple concentric rings of illumination from which light is directed toward the center of the rings. In operation, the area of interest on the microcircuit assembly is placed directly under the focused center of these concentric rings. The angle of incidence for each of these rings is unique, one for interconnect bond wires and ball bonds, while the other is for bond wedges. The combination of both rings is used for isolating microcircuit chips. As light is transmitted via the first ring, an annular layer of illumination is transmitted and focused onto the microcircuit surface from a predetermined angle of incidence. Light from this angle of incidence reflects off the specular surface of the bond wires and ball bonds, presenting unique reflective signatures to a dual magnification video camera system. Similarly, when a second ring is energized, unique reflective signatures (and background contrast) on the bond wedges are created. In accordance with this disclosure, information gathered from such illuminations is utilized to locate any selected conductor bond and determine a targeting site on that bond. An optical wave generator is then precisely aimed for impinging on the target on the bond. An optical detector is also aimed at some location offset from the bond.

In accordance with the parent disclosures, it has been determined that optimal angles of incidence relative to the reflective surface can be found for different classes of objects. Since the reflective surface of a bond wire is cylindrical, for instance, illumination from any angle should produce the same reflective result to the video camera. Limitations arise however, when one has to consider the gold conductor traces the bond wires have to bridge over. These conductor traces form a gold background which has approximately the same reflective angle as the gold wires, thereby causing the bond wires to "disappear" into their background. It was found that by lowering the angle of transmission to between 75 and 85 degrees from the vertical axis, light reflected from conductor trace surfaces is directed away from the video camera, while the light reflected from part of the cylindrical surface reflects directly to the video camera, providing a significant contrast between the bond wires over the conductive traces.

In the case of wedge bonds, the physical feature is quite different than that of the cylindrical surface of a bond wire. Its features result from the stamping process in which the bond wire is pressed onto the gold surface by the capillary tube of a typical wire bonding machine. This stamping process flattens part of the cylindrical wire forming a flat reflective surface at the wedge site. This flattened reflective surface changes from the slope angle of the wire to that of the horizontal surface of the substrate. This sloped surface provides a mirror-like reflective surface as well as a unique signature compared to that of a bond wire. It is expected that the optimal angle of light transmission will be different relative to the round wire. It has been found that, by shifting the light transmission angle to between 25 and 35 degrees from the vertical axis, optimal contrast between the wedge reflective surface and the conductive traces can be obtained.

Preferred formation of the multiple light rings starts with light generated by a tungsten lamp, collimation of such light by a condenser lens, then passage through a liquid crystal light valve having a plurality of circular active transmission areas. A projector lens receives both rings of light and projects the larger ring on an ellipsoidal reflector which redirects the light onto the microcircuit at the large off-vertical axis angle. The projector lens also focuses the more narrower diameter beam of light on a torroidal Fresnel lens mounted above the microcircuit which directs such beam at the smaller off-vertical axis angle.

By alternating or switching the light transmission through each of these rings at high speed electronically, reflective signatures of interconnect wires, ball bonds, bond wedges and solder joints can be captured by an objective lens and mirror reflected to light responsive transducers of the camera system. Based on known light speed and distances between the transmission source and light responsive cameras, elapsed time between transmission to image capture is calculated to be 3 nanoseconds. The disclosed approach permits the alternating of illumination sources in less than 4 milliseconds using the computer-controlled liquid crystal and reflector system. The speed of highlighting microelectronics components is therefore limited by the performance speed of managing illumination transmission through each of the light ring sources.

A dual magnification viewing system was developed using beam splitters and reflectors such that both calibrated high and low magnification images are presented to two separate video cameras at the same time. Such, in part, comprises photodetector mean for detecting reflective signatures emanating from the substrate resulting from the above described switching of the light valve. By selecting the images electronically by the following vision system, the switching of high and low magnification can be obtained in 1 millisecond the high or low magnified images can be acquired in 33 milliseconds.

BALL BONDS AND WEDGE BONDS

Figure 2:
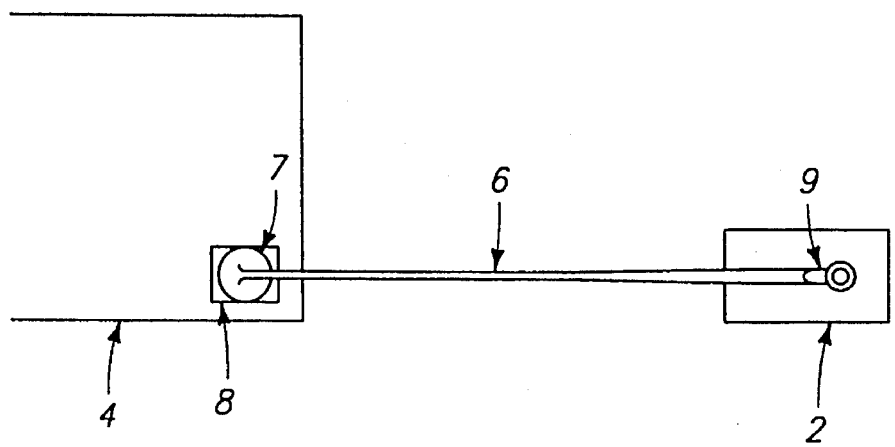
FIG. 2 is a partial top view of the typical interconnection depicted in FIG. 1.

Appreciation of aspects of this invention starts with an understanding of common interconnection methods used in microelectronic assemblies. Referring to FIGS. 1 and 2, a microcircuit assembly 1 includes a conductive circuit pattern 2 printed on the surface of a base substrate 3, usually made of a ceramic material. A cubed shaped microcircuit chip 4 is attached onto substrate 3 using conductive or non-conductive epoxy 5. The electrical connection between the microchip circuit and the conductive traces on the substrate is made via a cylindrical gold wire conductor 6, typically 0.001 inch in diameter. The attachment of one end of the wire onto the microchip surface takes the shape of a flattened gold ball 7, correspondingly termed a ball bond. The bonding site for this attachment is called a bond pad 8, and normally is a square conductive pad, situated atop microchip 4.

The opposite end of wire 6 is attached onto the surface of substrate conductive trace 2 by a stamping process, which results in the form of a flattened wedge 9, correspondingly termed a wedge bond. Since the surfaces of microchip 4 and conductive pad 2 are at different heights, bond wire 6 takes the form of a wire loop 10 between the two connections. This loop assures that bond wire 6 is prevented from touching the edge of the microchip 4, as well as providing adequate stress relief for the bond wire in the event of severe thermal stress and vibrations.

Though ball bonds 7, bond wires 6, and bond wedges 9 are unique in their physical shape, each possesses highly specular outer surfaces. Aspects of this invention take advantage of these highly specular surfaces and unique reflective signatures, and provides apparatus and methods for presenting these images to light responsive transducers at high speed.

Illumination Concepts

Applying known physics principles of reflectivity, for a reflective surface, the angle of reflection is equal to the angle of incidence measured from the axis perpendicular to the tangent of the surface. Under usual inspection circumstances, illumination is directed onto the microelectronics surfaces perpendicularly. Light striking bond wires, ball bonds, and bond wedges scatters in all directions due to the specular and cylindrical surfaces. The gold conductor traces lying in the background also produce scattered light rays. The majority of these are directed vertically back toward the light source because the conductor trace surfaces are relatively flat. These reflected light rays are the main causes of misinterpretation of images by imaging machines as well as human operators. An aspect of the parent disclosures is the determination of the optimal angles of incidence for bond wires, ball bonds and wedge bonds, such that maximum contrast between the objects and their neighboring background can be achieved.

Figure 3:
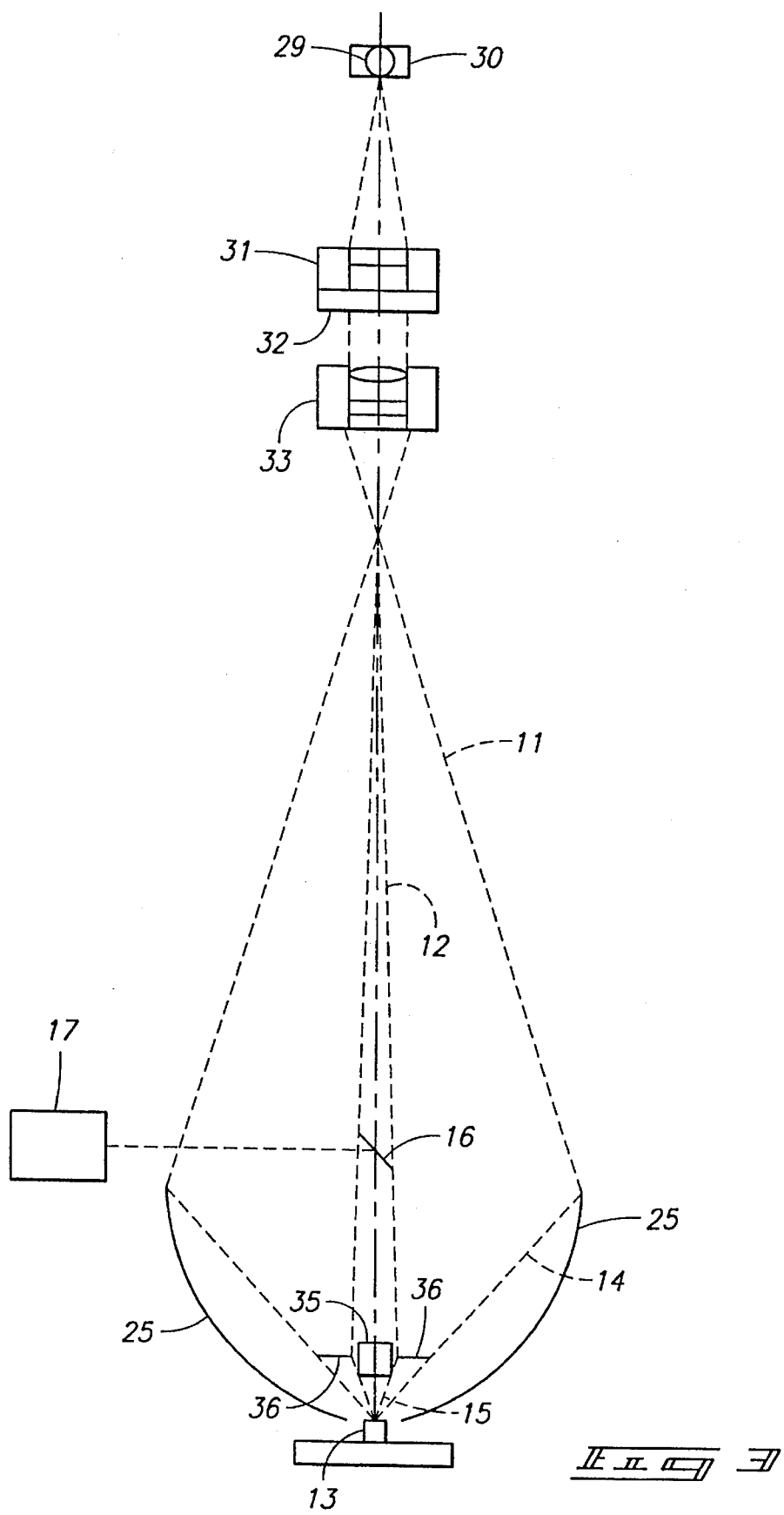
FIG. 3 is a side cross-sectional view of an arrangement of optical elements of an illumination system.

Referring to FIG. 3, preferred aspects of this invention include two light sources 11 and 12 affixed at desired angles of incidence from an object of interest 13 such that their respective reflected light rays 14 and 15 (reflected off reflector 25) strike the object of interest at the desired angles. Such light reflects off object 13 and onto a mirror 16 to a charge coupled device (CCD) array of solid state camera system 17. By feeding light into these sources sequentially or simultaneously, different objects can be highlighted. For example, to highlight bond wires and ball bonds, light source 14 at 75° to 85° is illuminated. On the other hand, if illumination of wedge bonds is desired, light source 15 at 25° to 35° degrees is illuminated. Similarly, if the overall chip is to be highlighted, both the light sources are illuminated.

The basic optical design of the illumination system is also shown in FIG. 3. Light from a filament 29 of lamp 30 is collimated by a cemented doublet condenser lens 31. Condenser lens 31 is positioned one focal length from lamp 30, thus collimating light from the lamp's filament 29. The degree of collimation is set by the size of the filament 29.

Figure 4:
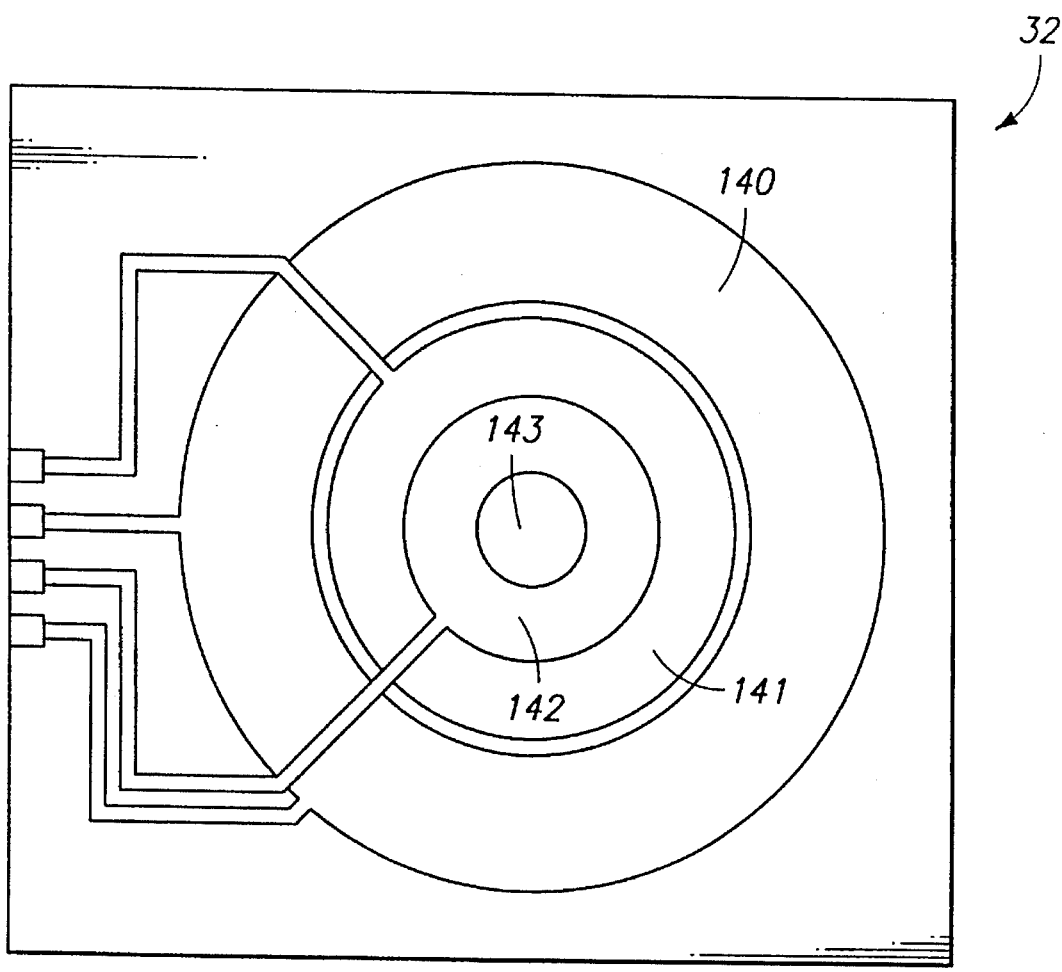
FIG. 4 is a top view of a concentric ringed liquid crystal light valve.

FIG. 4 diagrammatically illustrates a top view of a liquid crystal light valve 32. Such is placed just beyond condenser lens 31 (FIG. 3). Valve 32 has individually addressable or switchable concentric circular active regions 140, 141 and 142, and a central constantly opaque region 143. Such enables multiple distinct radial zones of light to propagate through the remainder of the illuminator system. Regions 140, 141 and 142 each constitute switchable twisted nematic LCD cells. In the natural or neutral state, the liquid crystal cell twists the passing light 90 degrees. However, the twisting power can be nullified by applying an electric field. Therefore, light valve 32 can be turned on and off directly by electronic means.

The output of liquid crystal valve 32 is imaged by a biconvex and cemented doublet projector lens 33 (FIG. 3) onto an elliptical reflector 25 for production of larger incidence angle 14. The angle of arrival of the illumination light from reflector 25 relative to a normal to the object surface is between 30 and 82.5 degrees. Since elliptical reflector 25 is not capable of producing angles of incidence less than approximately 50 degrees, a second optical system is used for the smaller angles. Specifically, a pair of Fresnel lens elements 36 redirects light source 12 via rays 15 onto microcircuit 13 at smaller angle.

The function of projector lens 33 is to image the condenser lens 31, or a plane just in front of it, onto the surface of reflector 25. The light which enters the projector lens 33 is nearly collimated and hence the stop is outside the projector lens. The projector lens 33 therefore takes on some of the characteristics of an eyepiece.

Reflected light from the microcircuit workpiece 13 is co-linearly collected above the workpiece, is focused and redirected to camera system 17 by means of objective lens 35 and mirror 16. This arrangement provides flexibility in off axis placement of the camera elements.

Using the above apparatus and angles of illumination, highlighted bond wires have an image signature of a highlighted wire, ball bonds take the shape of a highlighted ball, while bond wedges take a lighted shape similar to a triangle, and a microchip takes the shape of a black block among white surroundings when projected onto a video monitor via a video camera. By using the threshold function of a machine vision system, the entire wire span, ball bonds and wedge bonds in a field of view can be further isolated from background.

The parent disclosures describe an automated viewing system which is preferably utilized in accordance with aspects of this disclosure. Such discloses a dual magnification system used for high speed switching of two different magnifications. This dual magnification system is also preferred in accordance with this disclosure to pinpoint the exact target on the area of interest such that a laser pulse is directed to impinge at a precise location.

Using the above features and components, location and size of any selected conductor bond can be determined. Such information can then be used to accurately position one or both of the substrate or an optical elastic wave generation apparatus to precisely aim optics onto the conductor bond to generate an elastic wave. Such will now be more fully described.

In accordance with the actual determination of adherence integrity in accordance with the invention, an elastic wave is optically imparted onto and through the microelectronic conductor bond of interest and into the substrate therebeneath. An elastic wave signature will emanate from the substrate resulting from the optically imparting step, and will be detected by some suitable means. The emanated signature will be indicative of the bond size and quality. Using previously known or determined parameters as to bond area size, the signature directly provides data indicative of bond quality.

The preferred methods for both imparting an elastic wave and determining a signature emanating from the substrate is by using lasers to generate and detect ultrasonic waves passing through the bond. A technique for imparting ultrasonic waves onto an object using a laser and measuring an elastic wave emanating therefrom also using lasers is disclosed in our U.S. Pat. No. 5,103,676. Such is hereby fully incorporated into this document by reference.

Specifically, surface waves are generated in the substrate at the bond interface, and are subsequently detected at a nearby substrate surface point by optical means. The method is non-contacting and can be conducted utilizing only optical access to the surface of the conductor bond under analysis.

Figure 5:
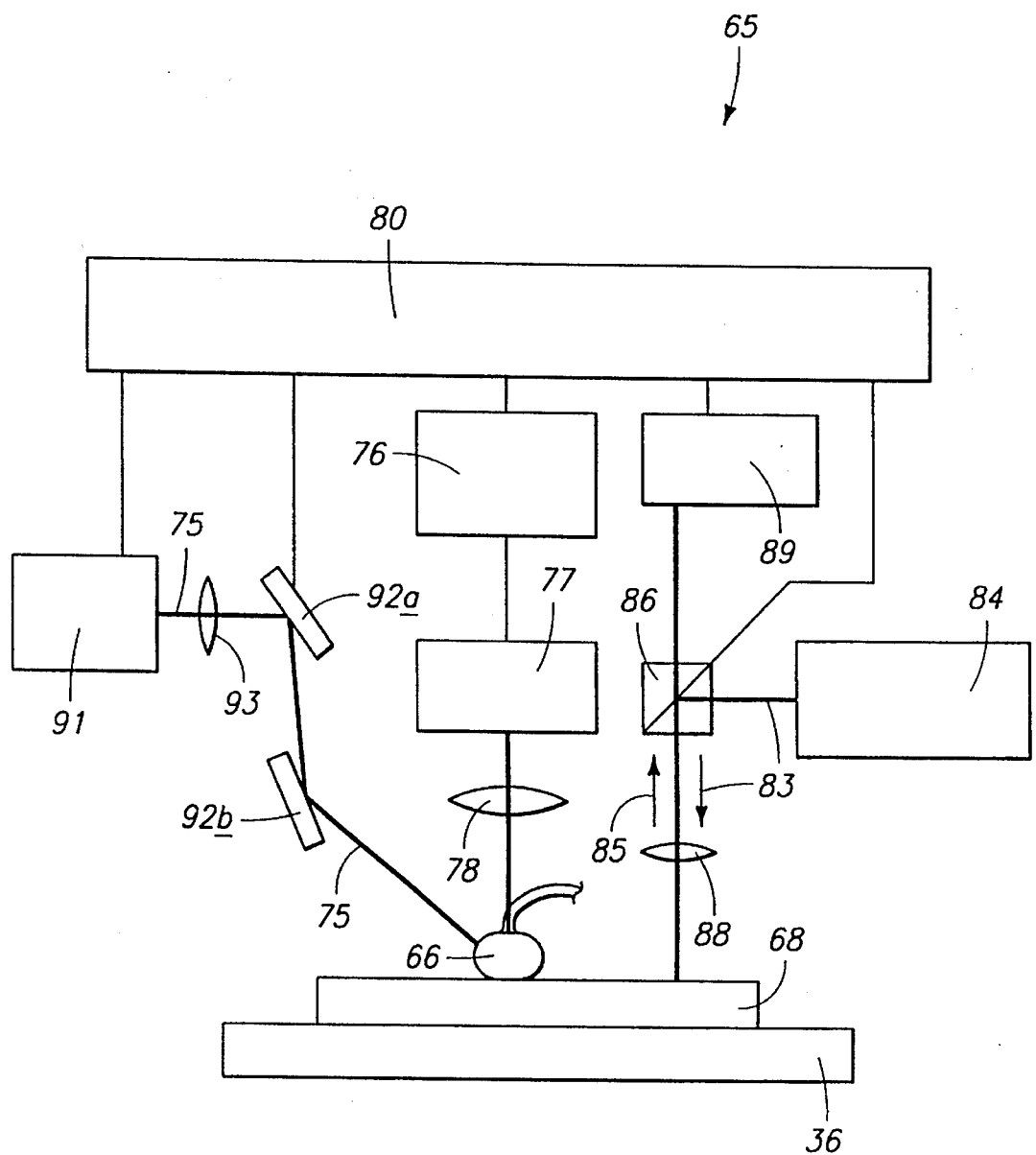
FIG. 5 is a block diagram of integration of subassemblies into an automated conductor bond integrity analysis system.

Referring to FIG. 5, a system for evaluating integrity of microelectronic conductor bonds to a substrate is indicated generally with reference numeral 65. Analysis is being conducted of a selected microelectronic conductor wire bond 66 which adheres to a semiconductor substrate 68. Such is positioned and supported by an XYZ transport stage 36, as described in the parent disclosures. Component 91 is a pulsed laser, such as an Nd-YAG laser. Component 93 is a focusing lens system. Components 92a and 92b are a pair of mirrors which are controlled to be independently rotatable about respective axes of rotation which are perpendicularly oriented relative to one another. In the illustrated embodiment for example, the axis of rotation of mirror 92a would be perpendicularly oriented relative to the plane of the FIG. 5 sheet, while the axis of rotation of mirror 92b would be parallel with the plane of the FIG. 5 sheet. Such enables essentially any point on ball bond 66 to be targeted for laser impinging. Collectively, such comprise wave propagation means and aiming means for ultimately directing light in the form of laser beam 75 onto selected microelectronic conductor bond 66.

Substrate 68 containing one or more conductor bonds is imaged with a CCD camera and image-capturing electronics 76 through an illumination control device 77 and optics 78, as generally described above and in the parent disclosures. Such will be utilized to very precisely determine and locate a target site on the selected conductor bond 66 through the overall system controller 80. Such will also positionally adjust laser beam steering mirrors 92a and 92b to accurately direct laser beam 75 onto the determined target on conductor bond 66. Such is described in more detail below.

Once conductor bond 66 is precisely located, the target determined and the laser optics are accurately aimed, laser 91 fires a pulsed beam 75 as directed by a PC based system controller 80 and ultimately onto conductor bond 66. The thermoelastic generation mechanism for ultrasonic waves produces wave amplitudes proportional to the power absorbed by the laser pulse. Therefore, short pulses (typically 10 to 50 nanoseconds) are desired to obtain high generation efficiency. In order to achieve a significantly large thermoelastic expansion of the conductor bond without causing damage, the pulsed power density at the conductor bond is preferably at approximately the ablation threshold of the bond material, such as at about 20 MW/cm$^2$ for aluminum or 100 MW/cm$^2$ for gold.

For example, the size of a typical ball bond is eighty microns in diameter, presenting a surface area of $5 \times 10^{-5}$ cm$^2$ to the impinging radiation. The laser beam pulse will effectively be spread out over the entire area of the bond. For a bond area of $5 \times 10^{-5}$ cm$^2$, this corresponds to an input power of around 1.0 KW, which corresponds to about 10 millijoules of energy per pulse at a pulse duration of 10 nanoseconds. These values are of course dependent on the particular ball material used and the laser pulse duration. Wavelengths of the laser radiation are not believed to be critical, thus allowing infrared or visible lasers to be used.

Thermoelastic expansion of the bond causes elastic waves to travel through the bond and into substrate material 68. At the bond interface, resulting elastic stress is transmitted to the substrate (for a good bond) and acts as a source for generation of bulk and surface waves in the substrate. The amplitudes of the waves generated in the substrate are proportional to the amplitude of the elastic bond stress and the area of contact at the bond. Therefore, a quantitative measure of bond quality/integrity is determinable from the wave signature emanating from the substrate.

Partial or non-bonds would alter the contact area and proportionally change the elastic wave amplitudes which are generated. Either bulk or surface waves in the substrate can be recorded to obtain a measure of bond quality, but use of the surface alone would allow only single-sided measurement of bond quality. In the substrate, numerous reflections of the waves are generated by the various boundaries. Yet, if the first transit of wave is captured before it hits a boundary, a signal directly proportional to the bond quality is obtained.

At a set distance away from conductor bond 66, the surface wave generated at the bond is detected by a non-contacting optical method employing components 84, 86, 88 and 89. The detection method consists of directing a laser beam 83 from a laser source 84 onto the surface of substrate 68 through a beam positioning device 86. An example laser would be a frequency stabilized He-Ne laser. The reflected beam 85 is directed through focusing and collection optics 88 through positioning/splitting device 86, and to a suitable detector 89. Example techniques for performing such methods are disclosed in U.S. Pat. No. 5,103,676.

The detection beam is focused to a size smaller than the conductor bond area. Shot noise limited detection on gold reflecting surfaces can be achieved with power densities at the surface on the order of 200 W/cm$^2$, which is too low to cause any surface damage. For example, a typical ball bond is 75–80 microns in diameter, and there is usually an unused pad or substrate area near the ball. Preferably, the detection point is typically 100 to 300 microns from the center of the ball. This distance is variable and determined by the accessibility of the neighboring area. Since a typical surface wave on the substrate travels at around 3 millimeters per microsecond, this surface wave will take approximately 30 to 100 nanoseconds to reach the detection point. This elastic energy can be measured by a suitable optical ultrasonic detector, and a fast transient recorder. The detector can consist of either a knife-edged position sensitive photodetector, or an interferometer with detection electronics. Interferometry techniques such as homodyne, heterodyne, or time delay or Fabry-Perot are examples.

Thermoelastic generation of an ultrasonic wave from laser absorption is known to occur from the surface volumetric expansion that is proportional to the absorbed energy. For a delta function input laser pulse, the volumetric expansion is essentially a step function. This step volumetric expansion generates surface waves similarly to a forced dipole located at the surface with the same time dependence, resulting in a bipolar wave of very high frequency content. However, two effects broaden the resulting surface wave time dependence. First, the laser pulse is of finite duration (typically 10 to 50 nanoseconds). Secondly, the area of absorption is finite (typically limited to the ball bond area). The result of these effects is to broaden the wave shape bringing down the frequency content of the wave to the 10–40 MHz region. This is still considered as a fast wave shape, requiring a transient recorder of approximately 10 nanoseconds digitization time for good signal recovery.

The use of laser ultrasonics in a microscopic environment is limited by the focusing of the source to the ablation threshold of the material. The thermoelastic wave amplitude is proportional to the laser pulse power absorbed at the surface. However, the limitation that the laser power density be comparable to the ablation power density means that the maximum useable power decreases as 1/(spot diameter)$^2$. Conversely, the close proximity of the detection point to the source point means that a larger signal will be observed compared to further away points by the square root of the distance. Therefore, the magnification decreases the useable signal due to the power density limitation but also increases the signal due to the close proximity between source and detector.

An estimate of this limitation can be found by comparing generation and detection at a larger scale to that at the microscopic scale. Published measurements on steel exhibited a surface wave peak amplitude of about 3 Angstroms at a separation of 65 mm using a pulse power density of 20 MW/cm$^2$ (energy per pulse of 6.0 millijoules, power of 0.60 MW) over a source area of 0.03 cm$^2$. Comparing this same pulse power density for a new source area of $5 \times 10^{-5}$ cm$^2$, corresponding to a ball of 80 micrometers diameter, the energy per pulse becomes 0.01 millijoules and the power becomes 1000 W. If the new separation is 108 micrometers, corresponding to a magnification of 600, then the new surface wave peak amplitude is related to the old amplitude by being proportional to the pulse power ratio (or pulse energy ratio) and being inversely proportional to the square root of the separation ratio, as the surface wave decreases inversely with the square root of the separation. This predicts a peak surface wave amplitude of 0.12 Angstroms for steel.

It is expected that the ablation power for gold will be slightly higher than for steel, and therefore wave amplitudes would be a little higher. For instance, using a power density of 100 MW/cm$^2$ (causing minor ablation), the displacement amplitude would be about 0.60 Angstroms. This is about the minimum detectability for an interferometer with sensitivity of $10^{-4}$ Angstroms/Hz$^{(1/2)}$ with a 40 MHz bandwidth. Increasing the detector sensitivity with more power, ablating slightly, or using a smaller separation distance, can all increase the bond signal. This estimate indicates that detection of the bond signal is feasible, and can be done with acceptable signal to noise ratio using an appropriate interferometer.

Alternate techniques might also of course be utilized to measure the elastic stress wave emanating from a substrate. By way of example only, such techniques would include capacitive measurement or use of piezoelectric transducers.

As alluded to above, target location or target siting for the laser on the bond of interest constitutes an important aspect of the invention. It is highly desirable that the laser pulse strike a ball bond, for example, at a controlled center or controlled location. Such is preferably determined using the above-described equipment and analyzing reflective signatures from the bond of interest. The preferred technique is to use the reflection pixels of the reflective signatures to define a straight-sided, two-dimensional window which entirely encompasses the conductor bond being analyzed. Utilizing the above-described techniques, a ball bond for example will produce reflection pixels which are distinguishable from its neighboring background which can be utilized in defining such a window. The two-dimensional window will have at least one x-coordinate side which is coincident with one extreme x-coordinate of the ball bond. The window will also have at least one y-coordinate side which is coincident with one extreme y-coordinate of the ball bond. Generation of such a window will enable determination of the shape and orientation of the selected conductor bond, if such shape is not previously known. Such further enables determination of the layout (such as size, dimension, orientation, etc.) of the conductor bond relative to the window.

Figure 6:
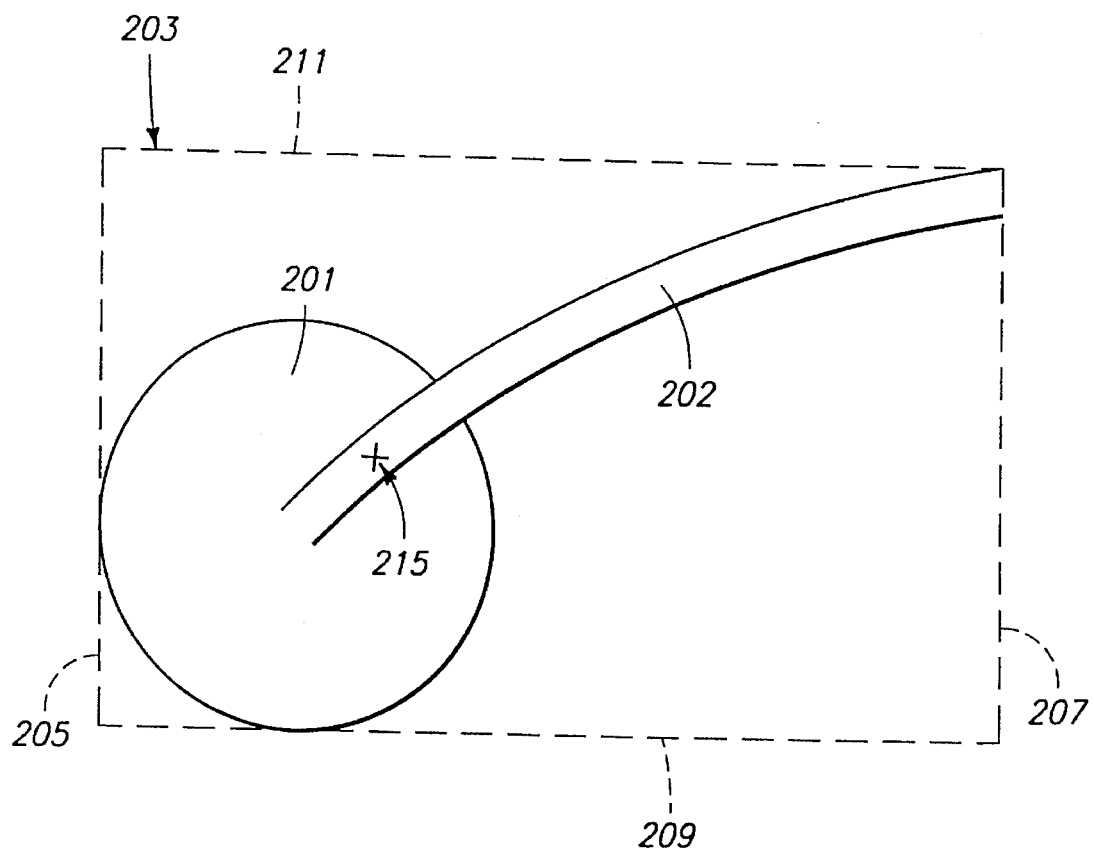
FIG. 6 is a top view, diagrammatic representation of targeting methods in accordance with aspects of the invention.

The location of the ball bond within the window is determined from the reflection pixels and conductor bond shape. From this, a precise desired target site on the ball bond can be determined. For example with reference to FIG. 6, assume a ball bond is being analyzed and its presence has been determined using the above illumination system. Using the above image processing technique, the top-most, bottom-most, left-most and right-most pixel locations of the ball bond are determined. These pixel locations are then used to draw a window or boundary encompassing the entire ball bond.

Specifically, a substantially spherical ball bond 201 and its associated bond wire 202 are shown. A window 203 is then created using processor 80 of FIG. 5. Window 203 includes one extreme x-coordinate side 205 which is coincident with the extreme far left illuminated portion of ball bond 201. An opposing extreme x-coordinate side 207 of the illuminated ball bond and wire is also determined. Window 203 also includes a lower extreme y-coordinate side 209 which is coincident with the extreme lower illuminated portion of ball bond 201. An opposing extreme y-coordinate side 211 of the illuminated ball bond and wire is also determined.

From creation of such a window, the location of the selected conductor bond within the window is determined by viewing the reflection pixels. The centroid of ball bond 201 can then be utilized in defining a target site on the bond. Processor 80 would then control movement of mirrors 92a and 92b (FIG. 5) to precisely align the pulsed laser beam to strike the desired target site.

An alternate and preferred technique can be utilized which should require less processing time in determining the targeting location. For example with respect to a ball bond, its general shape and diameter are constant and known. Further, it is known that a trailing bond wire will extend from each ball bond. A predefined sized window can then be utilized which will be known to include the entirety of the illustrated ball bond 201 and at least some portion of trailing wire 202. The drawn window will include at least one x-coordinate side, and one y-coordinate side which is coincident with the x and y, respectively, extremes of ball bond 201. What will not be instantly known is in which corner of the predefined window the ball bond will be positioned. A determination, however, can quickly be made to determine a center of reflection pixel density within the window, such as the illustrated centroid 215. Its location relative to the closest window corner is then determined. Due to the asymmetric shape of the combination of a ball bond and its associated trailing wire, centroid 215 will always be located a distance from the center of the window, and accordingly be positioned closest to some corner of the window where the ball is located. Once the corner of the window in which the ball is located is known, the targeting location can be determined from previously known parameters. For example for a 0.003-inch diameter ball bond, the targeting site would be determined to be 0.0015 inches offset in each of the x and y coordinates from the particular corner of the window. In the event a different ball bond size is used, the offset distance from the window could be adapted accordingly. With respect to system speed, it is anticipated that the aiming or movement of the mirrors will be the step requiring the most time, and thus the speed-limiting factor.

Figure 7:
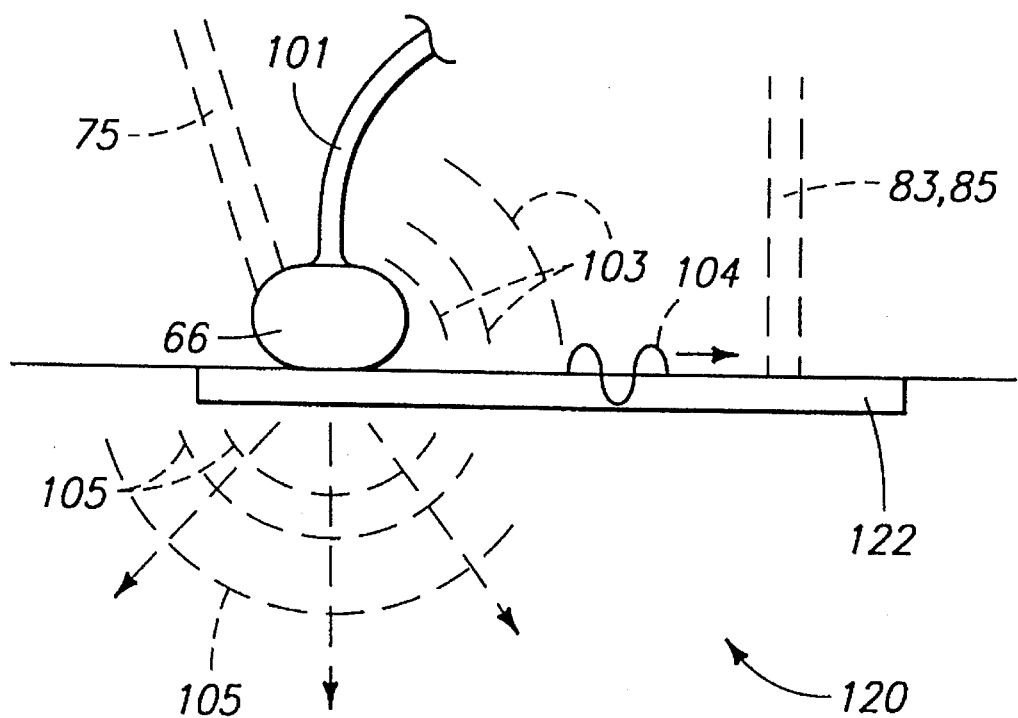
FIG. 7 is a diagrammatic representation of bond integrity measuring in accordance with the invention.

Some reduction-to-practice examples and considerations will become apparent from FIGS. 7–13. FIG. 7 illustrates a cross-section of a bulk semiconductor substrate 120 having a mating bonding surface or conductive bonding pad 122. A wire ball bond 66 and associated wire 101 bonds onto bond pad 122. An accurately aimed incident laser beam 75 generates an expanding acoustic airwave 103, a surface elastic wave 104, and a bulk elastic wave 105. Incident and reflective detection laser beams are shown diagrammatically as being superimposed, and are indicated with numerals 83, 85.

Figure 8:
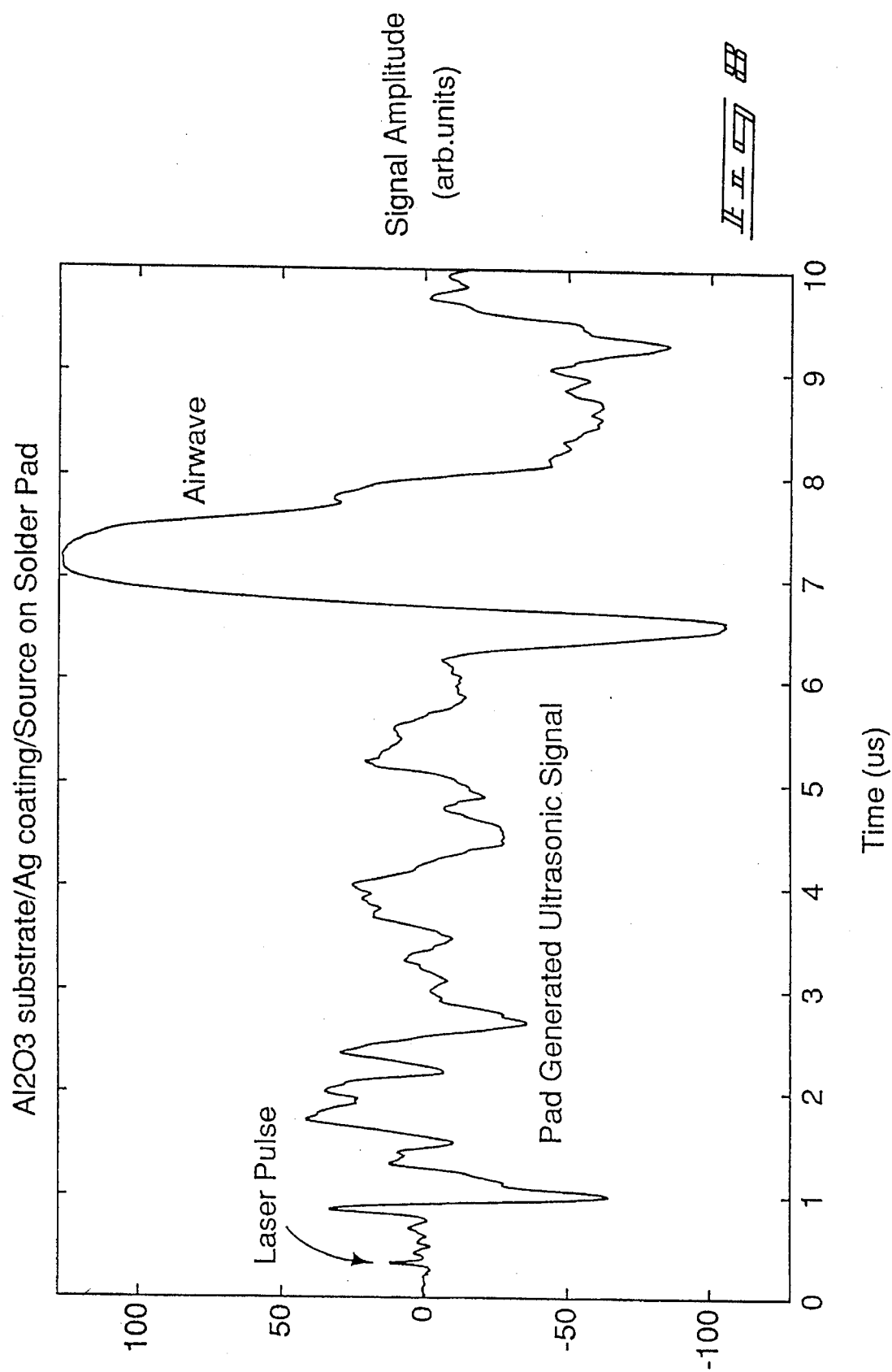
FIG. 8 is a plot of signal amplitude vs. time, as was experimentally reported in a reduction-to-practice method in accordance with the invention, in analysis of a FIG. 7 test.

FIG. 8 shows a plot of surface wave signal amplitude versus time of the ultrasonic elastic wave emanating from simulated ball bond 66 (FIG. 7) measured along the surface of the conductive bonding pad 122 by detection laser beams 83, 85. A unique waveform is produced for a subject bond between the time of the laser pulse, at about 0.4 microseconds in FIG. 8, and about 6 microseconds. The waveform generated at greater than 6 microseconds reflects the acoustic wave 103 which has passed through the air and traveled to detector beams 83, 85.

Figure 9:
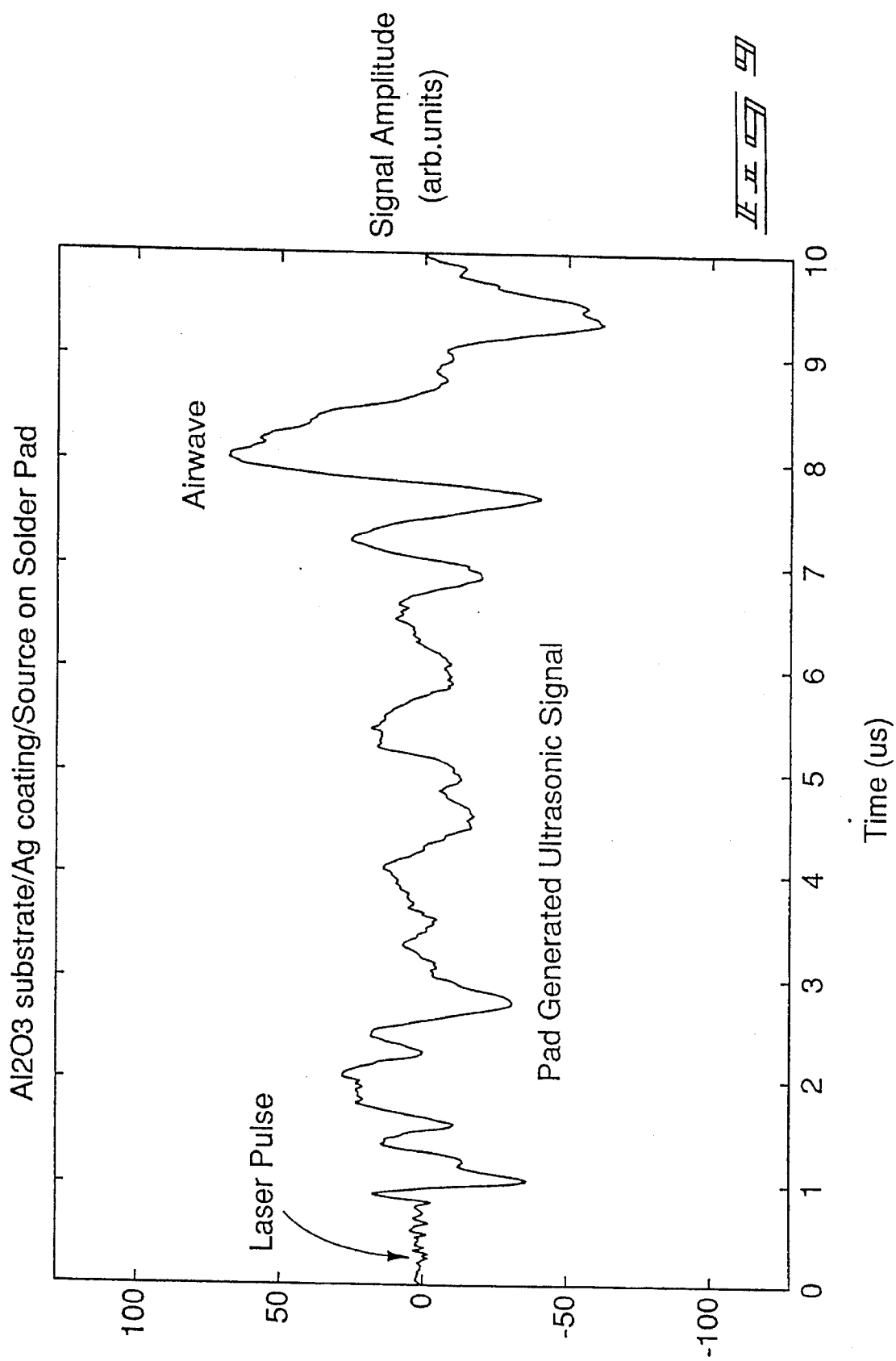
FIG. 9 is a plot of signal amplitude vs. time in analysis of another FIG. 7 test, as was experimentally reported in a reduction-to-practice method in accordance with the invention but using lower incident laser energy than that used in generation of the FIG. 8 data

FIG. 9 is another example of the same analyzed bond, as is diagrammatically depicted in FIG. 7, but at a lower incident laser power level.

Figure 10:
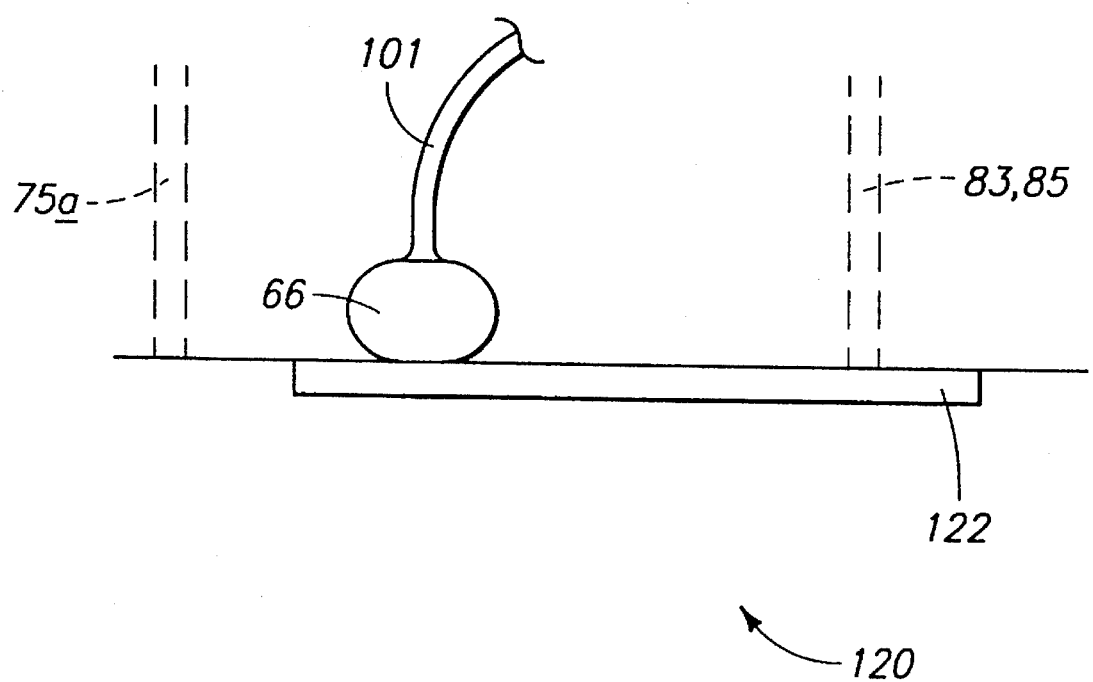
FIG. 10 is a diagrammatic representation of improper aiming in connection with a desired bond integrity measuring step.
Figure 11:
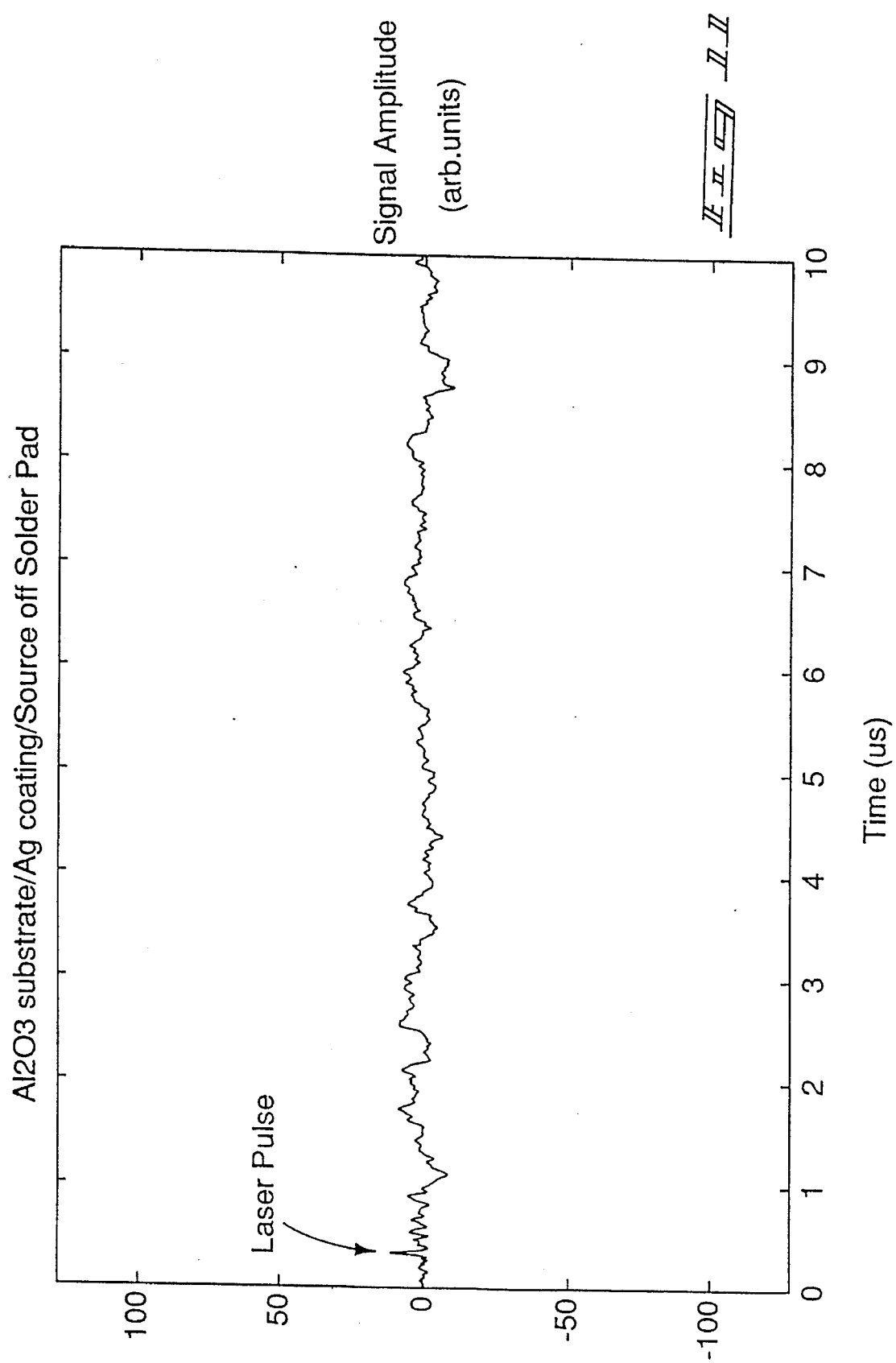
FIG. 11 is a plot of signal amplitude vs. time, as was experimentally reported, in analysis of the FIG. 10 test.

FIGS. 10 and 11 are provided to illustrate the signal detected by laser beams 83, 85 when an incident laser beam 75a was directed off of bond pad 122 and ball bond 66. FIG. 11 clearly indicates a drastically different waveform than that present in either of FIGS. 8 or 9, evidencing lack of signal due to the misaimed FIG. 10 method.

Figure 12:
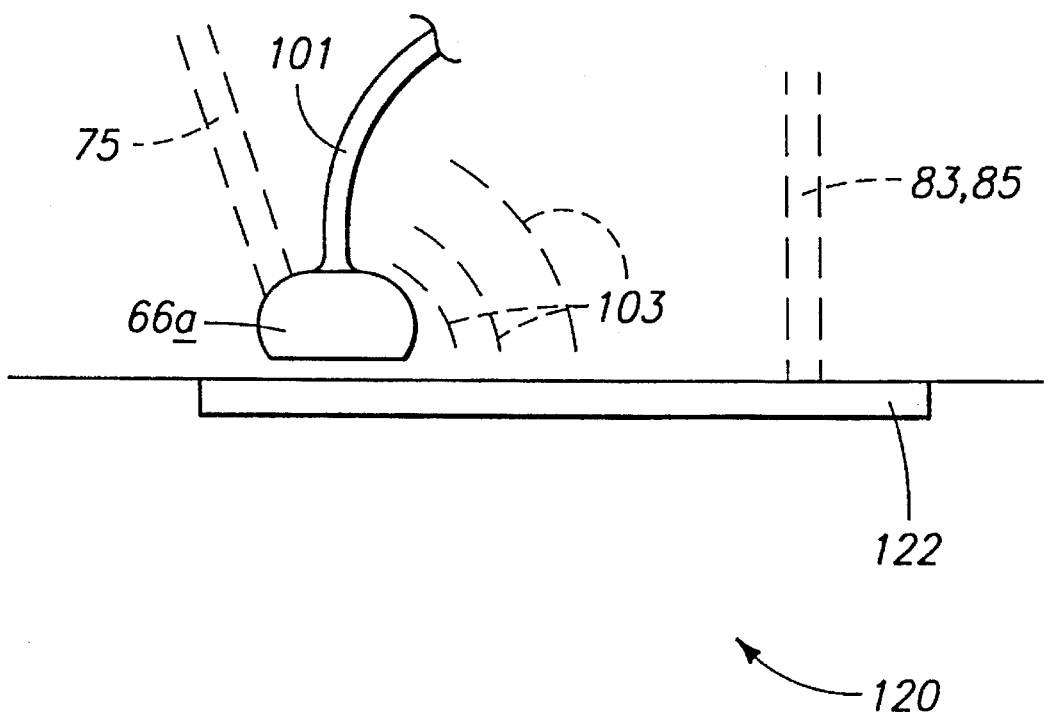
FIG. 12 is a diagrammatic representation of bond integrity measuring in accordance with the invention, with the conductor "bond" being analyzed having effectively no bonding to the substrate.

FIGS. 12 and 13 further illustrate analysis for a properly aimed laser beam 75, but against an effectively non-bonded ball bond 66a. FIG. 13 clearly shows a drastically different waveform signature from that of either FIGS. 8 or 9 from the point of laser pulse to airwave detection. FIG. 12 diagrammatically shows ball bond 66a not touching pad 122. The same essential result will however be reported if bond 66a were merely touching pad 122, but is not otherwise bonded to pad 122.

The above described preferred embodiments have been described with reference to evaluating integrity of adherence of ball bonds to an underlying conductive substrate. The invention however will have applicability to evaluating integrity of adherence of other conductor bonds to mating substrate surfaces. Examples include wedge bonds and solder joints.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method of evaluating integrity of adherence of a conductor bond to a mating surface on a substrate, the method comprising the following steps:

providing a plurality of ring light sources for illuminating a substrate and components adhered thereto;

focusing the ring light sources onto the substrate at respective selected angles of incidence relative to the substrate;

switching from one of the ring light sources to another of the ring light sources to optimize contrast of different objects on the substrate against background reflections;

detecting optical reflective signatures emanating from the substrate resulting from the switching step;

determining location of a selected conductor bond on the substrate from the detected reflective signatures;

determining a target site on the selected conductor bond from the detected reflective signatures;

optically imparting an elastic wave through the selected conductor bond and into the substrate;

detecting an elastic wave signature emanating from the substrate resulting from the optically imparting step; and determining integrity of adherence of the selected conductor bond to the substrate from the detected elastic wave signature emanating from the substrate.

2. The semiconductor processing method of claim 1 wherein the step of providing a plurality of ring light sources comprises passing light through a light valve having a plurality of active areas to form and switch individual rings of light.

3. The semiconductor processing method of claim 1 wherein the step of providing a plurality of ring light sources comprises passing light through a liquid crystal light valve having a plurality of switchable liquid crystal areas to form and switch individual rings of light.

4. The method of evaluating integrity of adherence of a conductor bond to a substrate of claim 1 wherein the steps of determining location and a target site comprise:

defining a straight sided, two-dimensional window entirely encompassing the selected conductor bond from reflection pixels of the reflective signatures, the two dimensional window having at least one x-coordinate side which is coincident with one extreme x-coordinate of the selected conductor bond, the two dimensional window having at least one y-coordinate side which is coincident with one extreme y-coordinate of the selected conductor bond;

determining or knowing the shape of the selected conductor bond;

determining location of the selected conductor bond within the window from the reflection pixels and conductor bond shape; and determining the target site on the selected conductor bond from the determined location of the selected conductor bond within the window.

5. The semiconductor processing method of claim 4 wherein the step of providing a plurality of ring light sources comprises passing light through a light valve having a plurality of active areas to form and switch individual rings of light.

6. The semiconductor processing method of claim 4 wherein the step of providing a plurality of ring light sources comprises passing light through a liquid crystal light valve having a plurality of switchable liquid crystal areas to form and switch individual rings of light.

7. The method of evaluating integrity of adherence of a conductor bond to a substrate of claim 1 wherein the steps of determining location and a target site comprise:

defining a straight sided, two-dimensional window entirely encompassing the selected conductor bond from reflection pixels of the reflective signatures, the two dimensional window having at least one x-coordinate side which is coincident with one extreme x-coordinate of the selected conductor bond, the two dimensional window having at least one y-coordinate side which is coincident with one extreme y-coordinate of the selected conductor bond;

determining or knowing the shape of the selected conductor bond;

determining a center of reflection pixel density within the window;

determining location of the center of reflection pixel density relative to a window corner;

determining location of the selected conductor bond relative to the window corner from the reflection pixel density center and conductor bond shape; and determining the target site on the selected conductor bond from the determined location of the selected conductor bond relative to the corner within the window.

8. The semiconductor processing method of claim 7 wherein the step of providing a plurality of ring light sources comprises passing light through a light valve having a plurality of active areas to form and switch individual rings of light.

9. The semiconductor processing method of claim 7 wherein the step of providing a plurality of ring light sources comprises passing light through a liquid crystal light valve having a plurality of switchable liquid crystal areas to form and switch individual rings of light.

10. A system for evaluating integrity of adherence of a conductor bond to a mating surface on a substrate comprising:

a plurality of ring light sources to illuminate a substrate and components adhered thereto;

focusing means for directing light from the plurality of ring light sources at respective selected angles of incidence relative to the substrate for contrasting between the substrate and components adhered thereto;

switching means for switching the directed light from one of the ring light sources to another of the ring light sources to optimize contrast of different objects on the substrate against background reflections as a result of the selected angles of incidence;

photodetector means for detecting reflective signatures emanating from the substrate resulting from operation of the switching means;

locating means for determining location of a selected conductor bond on the substrate from the detected reflective signatures;

wave propagation means for optically imparting an elastic wave through the selected conductor bond and into the substrate;

optical detection means for detecting an elastic wave signature emanating from the substrate resulting from operation of the wave propagation means; and processor means for determining integrity of adherence of the selected conductor bond to the substrate from the detected elastic wave signature emanating from the substrate.

11. The system for evaluating integrity of the conductor bond of claim 10 wherein the wave propagation means includes optical directing means for directing light onto the conductor bond, the wave propagation means further comprising aiming means for positionally adjusting the optical directing means after selected conductor bond location determination and before optically imparting the elastic wave.

12. The system for evaluating integrity of the conductor bond of claim 10 wherein the plurality of light sources and switching means comprise a light valve having a plurality of active areas to form and switch individual rings of light, the individual range of light comprising the plurality of light sources.

13. The system for evaluating integrity of the conductor bond of claim 10 wherein the light valve active areas are shaped to form a plurality rings having different widths.

14. The system for evaluating integrity of the conductor bond of claim 10 wherein the light valve active areas are shaped to form a plurality of circular and concentric rings.

15. The system for evaluating integrity of the conductor bond of claim 12 wherein the light valve active areas are shaped to form a plurality of circular and concentric rings, and wherein the focusing means comprises an encircling ellipsoidal reflector to receive and direct at least one of the circular and concentric rings at its respective incident angle.

16. The system for evaluating integrity of the conductor bond of claim 10 wherein, the plurality of light sources and switching means comprise a light valve having a plurality of active areas to form and switch individual rings of light; and the wave propagation means includes optical directing means for directing light from the plurality of light sources onto the conductor bond, the wave propagation means further comprising aiming means for positionally adjusting the optical directing means after selected conductor bond location determination and before optically imparting the elastic wave.

17. The system for evaluating integrity of the conductor bond of claim 10 wherein, the plurality of light sources and switching means comprise a liquid crystal light valve having a plurality of switchable liquid crystal areas to form and switch individual rings of light; and the wave propagation means includes optical directing means for directing light from the plurality of light sources onto the conductor bond, the wave propagation means further comprising aiming means for positionally adjusting the optical directing means after selected conductor bond location determination and before optically imparting the elastic wave.

18. A method of evaluating integrity of adherence of a conductor bond to a mating surface on a substrate, the method comprising the following steps:

impinging a plurality of light sources onto a substrate;

detecting optical reflective signatures emanating from the substrate from the impinged light;

determining location of a selected conductor bond on the substrate from the detected reflective signatures;

determining a target site on the selected conductor bond from the detected reflective signatures;

optically imparting an elastic wave through the selected conductor bond and into the substrate;

optically detecting an elastic wave signature emanating from the substrate resulting from the optically imparting step; and determining integrity of adherence of the selected conductor bond to the substrate from the detected elastic wave signature emanating from the substrate.

19. The method of evaluating integrity of adherence of a conductor bond to a substrate of claim 18 wherein the steps of determining location and a target site comprise:

defining a straight sided, two-dimensional window entirely encompassing the selected conductor bond from reflection pixels of the reflective signatures, the two dimensional window having at least one x-coordinate side which is coincident with one extreme x-coordinate of the selected conductor bond, the two dimensional window having at least one y-coordinate side which is coincident with one extreme y-coordinate of the selected conductor bond;

determining or knowing the shape of the selected conductor bond;

determining location of the selected conductor bond within the window from the reflection pixels and conductor bond shape; and determining the target site on the selected conductor bond from the determined location of the selected conductor bond within the window.

20. The method of evaluating integrity of adherence of a conductor bond to a substrate of claim 18 wherein the steps of determining location and a target site comprise:

defining a straight sided, two-dimensional window entirely encompassing the selected conductor bond from reflection pixels of the reflective signatures, the two dimensional window having at least one x-coordinate side which is coincident with one extreme x-coordinate of the selected conductor bond, the two dimensional window having at least one y-coordinate side which is coincident with one extreme y-coordinate of the selected conductor bond;

determining or knowing the shape of the selected conductor bond;

determining a center of reflection pixel density within the window;

determining location of the center of reflection pixel density relative to a window corner;

determining location of the selected conductor bond relative to the window corner from the reflection pixel density center and conductor bond shape; and determining the target site on the selected conductor bond from the determined location of the selected conductor bond relative to the corner within the window.

21. A system for evaluating integrity of adherence of a conductor bond to a substrate comprising:

a plurality of light sources to illuminate a substrate and components adhered thereto;

photodetector means for detecting reflective signatures emanating from the substrate resulting from operation of the light sources;

locating means for determining location of a selected conductor bond on the substrate from the detected reflective signatures;

targeting means for determining a target site on the selected conductor bond;

wave propagation means for optically imparting an elastic wave at the target site through the selected conductor bond and into the substrate;

aiming means for aiming the wave propagation means and substrate relative to one another for imparting the elastic wave onto the target site of the selected conductor bond;

optical detection means for detecting an elastic wave signature emanating from the substrate resulting from operation of the wave propagation means; and processor means for determining integrity of adherence of the selected conductor bond to the substrate from the detected elastic wave signature emanating from the substrate.

22. The system of claim 21 wherein the wave propagation means comprises a laser, and wherein the aiming means comprises a pair of mirrors independently rotatably mounted about a respective axis of rotation, the respective axes of rotation being perpendicularly oriented relative to one another.

* * * * *